(12) United States Patent
Bauer et al.

(10) Patent No.: US 8,790,576 B2
(45) Date of Patent: Jul. 29, 2014

(54) VESSEL TREATMENT MACHINE

(75) Inventors: Eva Bauer, Hamburg (DE); Frank Peter Behrendt, Pinneberg (DE); Margit Kiefer, Hamburg (DE); Andreas Kleiss, Norderstedt (DE); Bernd Neumann, Hamburg (DE); Andreas Stanislawski, Hamburg (DE); Hans Peter Stuwe, Reppenstadt (DE)

(73) Assignee: KHS GmbH, Dortmund (DE)

( * ) Notice: Subject to any disclaimer, the term of this patent is extended or adjusted under 35 U.S.C. 154(b) by 423 days.

(21) Appl. No.: 12/920,896

(22) PCT Filed: Mar. 10, 2009

(86) PCT No.: PCT/EP2009/001697
§ 371 (c)(1),
(2), (4) Date: Sep. 3, 2010

(87) PCT Pub. No.: WO2009/118096
PCT Pub. Date: Oct. 1, 2009

(65) Prior Publication Data
US 2011/0020176 A1   Jan. 27, 2011

(30) Foreign Application Priority Data
Mar. 25, 2008   (DE) .......................... 10 2008 015 675

(51) Int. Cl.
*A61L 2/00* (2006.01)
(52) U.S. Cl.
USPC ........................................... 422/28; 422/292
(58) Field of Classification Search
CPC .......... A61L 2/208; A61L 2/186; B65B 55/10
USPC ..................................................... 422/28, 292
See application file for complete search history.

(56) References Cited

U.S. PATENT DOCUMENTS

| 5,163,487 A | 11/1992 | Clusserath |
| 6,120,730 A | 9/2000 | Palaniappan |
| 6,478,240 B1 * | 11/2002 | Dorkin et al. ................. 239/433 |

FOREIGN PATENT DOCUMENTS

| DE | 1566670 | 4/1970 |
| DE | 3809852 | 10/1989 |
| DE | 10013150 | 10/2001 |
| DE | 10346843 | 6/2004 |
| DE | 10 2004 029803 | 1/2006 |
| EP | 0 353 486 A | 2/1990 |
| EP | 0 427 051 A | 5/1991 |
| GB | 2395904 A * | 6/2004 |
| WO | 01/68266 | 9/2001 |
| WO | 02/074351 | 9/2002 |
| WO | 03/030950 | 4/2003 |

* cited by examiner

*Primary Examiner* — Kevin Joyner
(74) *Attorney, Agent, or Firm* — Occhiuti & Rohlicek LLP

(57) ABSTRACT

The present invention relates to a vessel treatment machine for sterilizing containers (1) by means of a sterilization fluid and an associated treatment method. At least one fluid feed line (3) having at least one valve (5) disposed therein is provided to this end. One or more gas feed lines (4; 4*a*, 4*b*) are also present. Finally, a mixing chamber (7*b*) for producing a fluid/gas mixture is implemented. According to the invention, the mixing chamber (7*b*) and the outlet side valve chamber (7*b*) of the valve (5) work together functionally in fluid feed line (3).

20 Claims, 2 Drawing Sheets

VESSEL TREATMENT MACHINE

CROSS-REFERENCE TO RELATED APPLICATIONS

Figure 1:
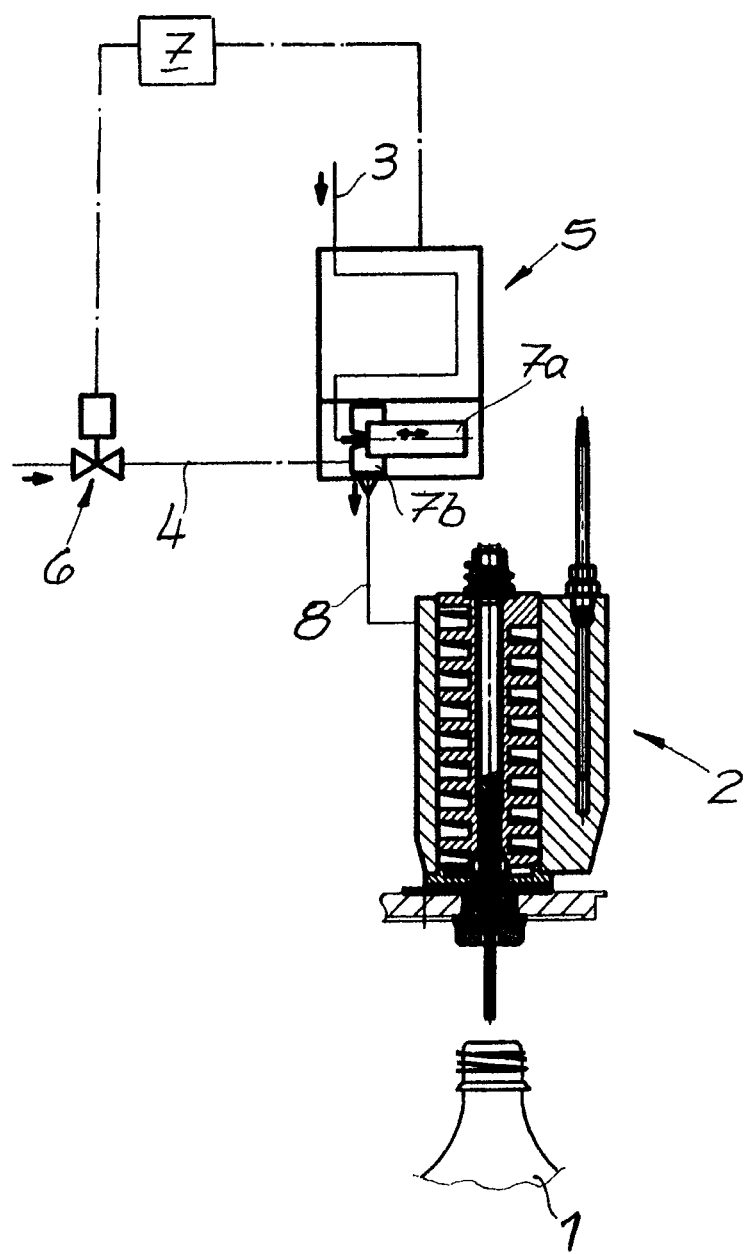

This application is the National Stage of International Application No, PCT/EP2009/001697, filed on Mar. 10, 2009, which claims the benefit of Germany Application Serial No. 10 2008 015 675.2, filed on Mar. 25, 2008, the contents of both of the foregoing applications are hereby incorporated by reference in their entirety.

The invention relates to a vessel treatment machine for sterilizing containers by means of a sterilizing liquid, said vessel treatment machine having at least one liquid supply line and one or more gas supply lines, in addition at least one mixing chamber for producing a liquid/gas mixture, and at least one valve in the liquid supply line.

Such a vessel treatment machine is described in the main in WO 03/030950 A1. Similar developments are the object of DE 10 2004 029 803 B4. The vessel treatment machine is routinely such a machine that is used in the beverage industry, i.e. as is used when filling beverages into bottles, cans or general containers that are made, for example, of plastics material, metal, glass etc.

For the most part such vessel treatment machines are connected upstream of a filling system and serve to ensure the necessary sterility inside the container and consequently the shelf life of the filled product. For this purpose, liquid hydrogen peroxide $H_2O_2$ is routinely added as sterilizing liquid in a finely atomized form to an air flow in the mixing chamber. Subsequently, said liquid/gas mixture or hydrogen peroxide/air mixture may be supplied to an evaporator in which the still liquid $H_2O_2$ is completely evaporated.

In reality it is necessary namely for the activation of the hydrogen peroxide, i.e. for its decomposition, to heat said hydrogen peroxide to a certain temperature. At said temperature, the hydrogen peroxide breaks down into water and free radicals, which are responsible for the actual sterilization. This has proven its value even in the sterilization of cardboard containers, as is described in principle in U.S. Pat. No. 6,120,730.

The perfect sterilization of containers presupposes that the sterilizing liquid is made available in a properly metered manner. This occurs in the majority of cases with the aid of the at least one valve present in the liquid supply line. However, the problem that arises in this case is that the amount of liquid forwarded by the valve, for example, to an atomizing device can vary from case to case. Said varying liquid amount can be explained by the sterilizing liquid that remains in the valve from one discharge cycle to another at a treatment head. Over and above this, possible additional so-called "dead amounts" in a supply line from the valve to the mixing chamber or as far as the atomiser have to be taken into consideration.—This is where the invention fits in.

The technical problem underlying the invention is to develop further a vessel treatment machine for sterilizing containers by means of a sterilizing liquid such that the sterilizing liquid is available in precisely meterable and reproducible amounts inside the mixing chamber.

To solve this technical problem, it is provided in the case of a generic vessel treatment machine that the mixing chamber and an outlet-side valve chamber of the valve coincide in an operative manner. I.e. the obligatory valve chamber at the outlet of the valve in the liquid supply line is used at the same time as a mixing chamber, i.e. for producing the liquid/gas mixture.

In this way, the gas entering the mixing chamber or the valve chamber is automatically responsible for ensuring that the valve chamber is flushed, as it were, at the desired mixing ratio. To this end, the gas supply line for the supply of the gas normally opens out directly into the outlet-side valve chamber. I.e. the valve chamber is used for atomizing the liquid/gas mixture and is thus emptied after each stroke.

Such a stroke corresponds to the necessary amount of liquid and gas that is necessary in most cases for the treatment of one container. As both the sterilizing liquid and the gas are supplied under pressure and the gas supply line can also be provided with a valve, it is possible by means of corresponding actuation of the valves to provide for the respective production of the liquid/gas mixture inside the mixing chamber or respectively valve chamber. Said liquid/gas mixture is then supplied to the treatment head, in which, as a rule, the already described evaporation operation and consequently the activation of the sterilizing liquid is effected. The activated sterilizing liquid or the mixture is finally blown into the container. This completes one stroke or operating stroke.

As, according to the invention, the metering operation takes places completely inside the outlet-side valve chamber of the valve representing the mixing chamber in the liquid supply line, the metering or the metering operation is separated from the evaporation operation and consequently is not time-critical. This means that the metering amount for the sterilizing liquid can be predetermined in a particularly sensitive manner, for example in terms of control. It is always guaranteed that the liquid/gas mixture subsequently leaving the outlet-side valve chamber or mixing chamber is adapted individually to the container to be treated.

The detail of this can be effected in such a manner that a valve body inside the valve in the liquid supply line opens an opening to a greater or lesser extent between an inlet-side valve chamber and the outlet-side valve chamber. When the position of the valve body is interrogated during this operation, the amount of sterilizing liquid metered into the outlet-side valve chamber can be predetermined precisely in terms of control. This occurs until the amount of sterilizing liquid present in this manner in the outlet-side valve chamber is sufficient for treating the associated container and for the subsequent atomization with the aid of the gas.

The valve body between the two valve chambers may then be closed and subsequently the valve in the gas supply line can be opened in order to atomize the amount of sterilizing liquid present inside the outlet-side valve chamber. Because this operation takes place directly in the outlet-side valve chamber, which functions at the same time as a mixing chamber, it ensures that, in the case of the atomizing operation described, all the liquid constituents of the sterilizing liquid enter into the liquid/gas mixture. Any dead amounts as in the prior art are not observed.

Further advantageous developments are described below. Thus it is conceivable to connect the outlet-side valve chamber of the valve located in the liquid supply line or respectively the control valve directly to a treatment head. However, it is also possible for the liquid/gas mixture generated in the outlet-side valve chamber to be supplied to an additional second mixing chamber, which is then connected, in its turn, to the treatment head. I.e. the mixing operation takes place in two stages, initially by the liquid/gas mixture being produced in the outlet-side valve chamber or first mixing chamber and then said liquid/gas mixture being transferred into an additional second mixing chamber, which is (also) acted upon with an additional second gas supply line. This means that the atomizing operation can be optimized. I.e. in this case, the additional second mixing chamber is supplied by the additional second gas supply line and a chamber supply line, which connects the first mixing chamber or outlet-side valve chamber to the second mixing chamber.

In order to accelerate the mixing operation even more, it is conceivable that the gas supply line is provided with a Venturi nozzle or generally with a nozzle on the inlet side of the (respective) mixing chamber.—As already explained, the valve in the gas supply line is also a control valve, that is a type of valve where the position of a valve body can be detected and in terms of control can be adjusted such that precisely the desired amount of metered gas or metered liquid (with the control valve in the liquid supply line) leaves the valve.

Generally speaking, the sterilizing liquid is liquid hydrogen peroxide, which is, however, not to be seen as compulsory. Sterile air is used predominantly as the gas, that is air that has been sterilized beforehand.—An object of the invention is also a method for sterilizing containers in accordance with Claim 10. The method described, in this case, can be accomplished in the vessel treatment machine explained in detail. However, this is not compulsory.

Figure 2:
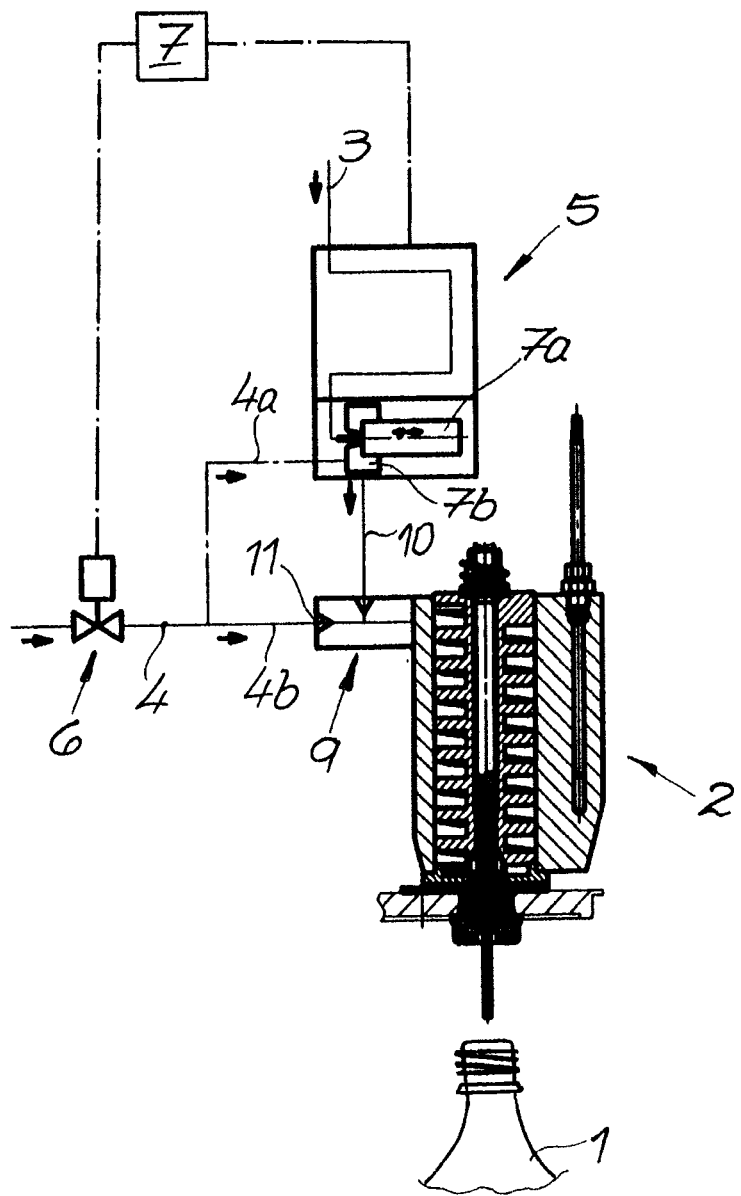

The invention is explained below by way of a drawing representing just one exemplary embodiment, in which, in detail:

FIG. 1 shows a first development of a vessel treatment machine according to the invention, reduced to the components essential to the invention and FIG. 2 shows a variant of the object in FIG. 1.

A vessel treatment machine which is used for sterilizing containers 1, is represented in the Figures. The container 1, just suggested in FIG. 1, is a plastic PET bottle, which is obviously not to be seen as limiting. The sterilization is effected with the aid of a liquid/gas mixture, which is to be activated in a container head 2, as is described in detail in DE 10 2004 029 803 B4. To this end, the container head 2 is provided, for example, with a heat exchanger, which is responsible for ensuring that the sterilizing liquid in the case in example is activated.

The sterilizing liquid in reality in the present case is liquid hydrogen peroxide but this is not compulsory, said hydrogen peroxide being supplied via a liquid supply line 3. Said sterilizing liquid or the liquid hydrogen peroxide is mixed with a gas (sterile air), which is supplied by way of a gas supply line 4. Inside the liquid supply line 3 there is a valve 5, which is in the form of a control valve. The gas supply line 4 also has a valve 6, which is also in the form of a control valve. The two control valves 5, 6 are connected to a common control unit 7, which interrogates the position of their respective valve body in order to make available, in terms of control, a metered amount of sterilizing liquid on the outlet side of the valve 5 and furthermore a metered amount of gas on the outlet-side of the valve 6. The gas is sterile air but this is not compulsory.

It can be recognised that the valve or control valve 5 is provided with an inlet-side valve chamber 7a and an outlet-side valve chamber 7b, which are separated from one another by a valve body. Depending on the position of said valve body, the amount of sterilizing liquid inside the outlet-side valve chamber 7b is predetermined—as described—in terms of control that is checked and predetermined by means of the control unit 7. As soon as the necessary metered amount of sterilizing liquid is present in the outlet-side valve chamber 7b, the valve body is generally closed and the valve 6 subsequently opened.

As the gas supply line 4 is connected to the outlet-side valve chamber 7b or opens out into said valve chamber, the outlet-side valve chamber 7b at the same time assumes the function of a mixing chamber 7b for producing the liquid/gas mixture or for the atomization of the sterilizing liquid in the interior of the outlet-side valve chamber 7b with the aid of the supplied gas. I.e. the mixing chamber 7b and the outlet-side valve chamber 7b coincide in an operative manner. It can be recognized that within the framework of the variant in FIG. 1, the outlet-side valve chamber or mixing chamber 7b is connected directly to the treatment head, namely by means of an output line 8. Contrary to this, in the case of the variant in FIG. 2 an additional mixing chamber 9 is realized.

In reality the gas supply line 4 is divided after the Venturi 6 into two separate gas supply lines 4a, 4b, which open out into the respective mixing chambers 7b or respectively 9 in the case of the variant in FIG. 2. In this case, the mixing chamber 7b or outlet-side valve chamber 7b of the valve 5 assumes the function of a first mixing chamber 7b, whereas the additional mixing chamber 9 operates as a second mixing chamber. The liquid/gas mixture generated inside the first mixing chamber 7b is supplied via a chamber supply line 10 into the second mixing chamber 9 and here experiences another mixing operation such that the additional gas supply line 4b is connected to the second mixing chamber 9.

In this case a Venturi nozzle 11 on the inlet side of the second mixing chamber 9 ensures that the gas supplied via the gas supply line 4b into the mixing chamber 9 experiences acceleration such that the atomization in the second mixing chamber 9 is intensified. The second mixing chamber 9 is connected directly to the treatment head 2, which is obviously not to be seen as compulsory. The treatment head 2 can itself be a component of a carousel-type machine or a linear machine, as is known in general.

Finally, it can be recognized that the sterilizing liquid in addition utilizes the natural gradient inside the liquid supply line 3 because the flow direction of the sterilizing liquid follows gravity. This means that optimum degassing of the sterilizing liquid can be achieved before said sterilizing liquid is mixed with the gas in the mixing chamber or first mixing chamber 7b. This guarantees that the liquid/gas mixture is composed in practice of only the two constituents—the sterilizing liquid and the gas (sterile air).

The invention claimed is:

1. An apparatus for sterilizing containers with a sterilizing liquid, said apparatus comprising a vessel treatment machine comprising a liquid supply line for conveying said sterilizing liquid, a first control valve in said liquid supply line, said first control valve defining an interior and an exterior thereof and comprising a first chamber located within said interior of said first control valve, a second chamber located within said interior of said first control valve, and a valve body disposed to separate said first chamber and said second chamber from each other, said valve body having a controllable position for controlling an amount of sterilizing liquid in said second chamber, and a first gas supply line disposed to enter said first control valve and to open into said second chamber within said interior of said first control valve for flushing said second chamber with gas, thereby enabling formation of an atomized mixture containing said sterilizing liquid.

2. The apparatus of claim 1, further comprising a heat exchanger connected to receive said atomized mixture and to activate said atomized mixture by applying heat thereto.

3. The apparatus of claim 2, further comprising a controller for periodically initiating and terminating an operating stroke during which a metered amount of sterilizing fluid passes from said first chamber to said second chamber, gas passes into said chamber, and said atomized mixture is blown out of said second chamber and enters said heat exchanger.

4. The apparatus of claim 2, further comprising a third chamber between said second chamber and said heat exchanger.

5. The apparatus of claim 4, further comprising a second gas supply line connected to provide gas into said third chamber, and a third gas supply line to convey said atomized mixture from said second chamber to said third chamber.

6. The apparatus of claim 4, wherein said third chamber is directly connected to said heat exchanger.

7. The apparatus of claim 4, further comprising a Venturi nozzle at an entrance to said third chamber.

8. The apparatus of claim 1, wherein said second chamber is directly connected to said treatment head.

9. The apparatus of claim 1, further comprising a Venturi nozzle for accelerating flow speed of gas in said first gas supply line.

10. The apparatus of claim 9, further comprising a Venturi nozzle for accelerating flow speed of gas in said second gas supply line.

11. The apparatus of claim 1, further comprising a second control valve in said first gas supply line for controlling gas flow therethrough.

12. The apparatus of claim 11, further comprising a controller for controlling said first control valve and said second control valve.

13. The apparatus of claim 12, wherein said controller is configured to move said valve body to cause said first control valve to provide a first metered amount of sterilizing liquid into said second chamber, and, following entry of said first measured amount into said second chamber, to open said second control valve to cause a second metered amount of gas to enter said second chamber.

14. The apparatus of claim 1, further comprising a container head connected to receive said atomized mixture.

15. The apparatus of claim 1, wherein said liquid supply line is oriented to cause liquid to enter said first control valve along a direction that follows gravity.

16. The apparatus of claim 1, further comprising a carousel, comprising heat exchangers for receiving said atomized mixture to activate said atomized mixture by applying heat thereto.

17. A method for use in a process for sterilizing containers using an apparatus that comprises a vessel treatment machine comprising a liquid supply line for conveying a sterilizing liquid, a control valve in said liquid supply line, said control valve defining an interior and an exterior thereof and comprising a first chamber located within said interior of said control valve, a second chamber located within said interior of said control valve, and a valve body disposed to separate said first chamber and said second chamber from each other, said valve body having a controllable position for controlling an amount of sterilizing liquid in said second chamber, and a first gas supply line disposed to enter said control valve and to open into said second chamber within said interior of said control valve for flushing said second chamber with gas, thereby enabling formation of an atomized mixture containing said sterilizing liquid, said method comprising causing a metered amount of sterilizing liquid to pass from said first chamber in an interior of said control valve into said second chamber within said interior of said control valve, and flushing said second chamber with gas, thereby creating said atomized mixture.

18. The method of claim 17, further comprising heating said atomized mixture.

19. The method of claim 18, further comprising causing said atomized mixture to enter a container for sterilization thereof.

20. The method of claim 17, further comprising adapting said metered amount to said containers to be sterilized.

* * * * *